(12) United States Patent
Vlass et al.

(10) Patent No.: US 6,210,639 B1
(45) Date of Patent: Apr. 3, 2001

(54) APPARATUS, METHOD AND COMPOSITION FOR CLEANING AND DISINFECTING

(75) Inventors: Elizabeth Gayle Vlass, Dunwoody; Christopher Roy Boam, Alpharetta, both of GA (US); Ian Michael Riorden George, Chester; Stephen Dennis Cooper, Flint, both of (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/179,138

(22) Filed: Oct. 26, 1998

(51) Int. Cl.[7] ........................................................ A61L 9/00
(52) U.S. Cl. .......................... 422/29; 252/186.3; 422/28; 422/30; 422/34; 435/1; 514/839; 514/840
(58) Field of Search .................................. 422/28, 29, 30, 422/34; 435/1; 252/186.3; 514/839–840

(56) References Cited

U.S. PATENT DOCUMENTS

| 4,095,877 | 6/1978 | Stoy | 351/160 |
|---|---|---|---|
| 4,670,178 | 6/1987 | Huth et al. | 252/95 |
| 4,743,447 * | 5/1988 | Le Rouzic et al. | 514/839 |
| 4,986,963 * | 1/1991 | Corcoran et al. | 422/30 |
| 5,045,222 | 9/1991 | Endo et al. | 252/102 |
| 5,378,475 | 1/1995 | Smith | 424/473 |
| 5,491,091 * | 2/1996 | Loshaek et al. | 422/30 |

FOREIGN PATENT DOCUMENTS

| 2 288 979 | 11/1995 | (GB) . |
|---|---|---|
| WO 98/37921 | 9/1998 | (WO) . |

* cited by examiner

*Primary Examiner*—Krisanne Thornton
(74) *Attorney, Agent, or Firm*—R. Scott Meece; Robert J. Gorman, Jr.

(57) ABSTRACT

Compositions and methods of disinfecting and cleaning medical articles are disclosed. Disinfecting contact lenses by generating of peracetic acid in situ, while simultaneously cleaning with a proteolytic enzyme, is a preferred embodiment. Tablets for simple consumer use including disinfecting and cleaning means, and delayed release neutralizing means, are also disclosed.

17 Claims, 2 Drawing Sheets

APPARATUS, METHOD AND COMPOSITION FOR CLEANING AND DISINFECTING

BACKGROUND OF THE INVENTION

1. Field of the Invention

This invention relates generally to disinfection and cleaning systems for medical devices. In a preferred embodiment, the invention relates to compositions, methods and articles for simultaneously cleaning and disinfecting contact lenses.

2. Description of the Related Art

The medical arts include a wide variety of systems for cleaning and disinfecting articles. Disinfectant systems range from the harsh, such as chlorine bleach for surgical tools, to the mild, preservative range, such as boric acid or quaternary ammonium polymers for contact lenses. Typically, a specific medical device and its use will dictate specific requirements for disinfecting and cleaning, although many requirements are common for all medical devices.

A particularly difficult field in which to design disinfecting and cleaning systems is the field of ophthalmics, which relates to articles which have intimate contact with ocular tissue and fluids. Ophthalmic articles include vision-correcting contact lenses, ocular wound healing coverings, intraocular lenses, ophthalmic drug delivery devices and the like. Clearly, ophthalmic article disinfecting and cleaning systems must balance several factors.

For example, contact lens cleaning and disinfecting systems must both sufficiently disinfect adhered microorganisms for safe use and sufficiently clean or remove adhered protein and lipids for good visual acuity. Also, consumer convenience is a major factor, requiring such systems to be rapid, involve minimal consumer manipulation, and be easy to store and transport. Of course, overall system cost is also a significant concern. In addition, lens polymer interactions must be minimized (e.g., disinfectant adsorption and release rates, lens discoloring, polymer decomposition, lens shape alteration and visual distortion). Moreover, ophthalmic compatibility is an overriding concern, and this compatibility includes not only cell toxicity but also ocular comfort. Furthermore, disinfectants may deactivate cleaners, and vice versa, or the operating conditions of each may not coincide. In view of these and other competing factors, development of a successful contact lens cleaning and disinfecting system is highly complex, and there remains a need for a system which balances all of these factors.

SUMMARY OF THE INVENTION

An object of the invention is to provide a simultaneous cleaning and disinfecting system for medical devices.

Another object of the invention is to provide a rapid, convenient, efficacious simultaneous cleaning and disinfecting system for contact lenses.

A further object of the invention is to provide a system for cleaning and disinfecting ophthalmic lenses in less than 30 minutes.

Yet another object of the invention is to provide a system for cleaning and disinfecting ophthalmic lenses which can be used with tap water.

One embodiment of the invention is a cleaning and disinfecting system which includes a dosage form or tablet which can be dissolved in a saline solution within a container. The dosage form includes a cleaning and disinfecting portion and a portion which neutralizes the cleaner and disinfectant. The disinfectant which is provided in the dosage form, or generated in situ, is peracetic acid.

In a preferred embodiment of the invention, the cleaning and disinfecting portion of the dosage form includes a peroxide-generating species and an N,N-diacylamide activator to generate peracetic acid in situ. The cleaning and disinfecting portion further includes effervescent additives to increase the dissolution rate and uniformity of concentration profile. Additionally, the cleaning and disinfecting portion includes an amount of enzyme sufficient to remove lipids and proteins from the article to be cleaned. The neutralizing portion includes means for neutralizing the peracetic acid and enzyme.

DESCRIPTION OF THE PREFERRED EMBODIMENTS

The present invention satisfies the long felt need for a simultaneous cleaning and disinfecting system which is convenient, safe, effective, rapid and inexpensive. While the system will be described in relation to a preferred use—its ophthalmic use (e.g., for contact lenses), the reader will understand that the system may be used on a wide variety of articles, and is especially advantageous for medical devices.

In general, one embodiment of the present invention is a solid dosage form or tablet which includes, without limitation, disinfectant or disinfectant-generating means, means for neutralizing the disinfectant, a cleaning agent, and means for neutralizing the cleaning agent. "Neutralization", as used herein, means deactivation sufficient to achieve ophthalmic compatibility.

In a preferred embodiment, the neutralization means is released only after a predetermined period of time during which the disinfectant and cleaning agent have operated at full strength. Thus, a preferred embodiment includes a means for delaying the release of the neutralizing means.

The disinfectant is peracetic acid, or an equivalent thereof, which can be released directly from the dosage form or generated in situ in a number of manners. A preferred method of generating peracetic acid in solution involves dissolving a peroxide or peroxide-generating species and an activator (e.g., an N,N-diacylamide activator) in solution. A preferred peroxide-generating species is an alkali metal perborate, such as sodium perborate. A preferred activator is tetraacetyl ethylene diamine (TAED).

Peracetic acid is most effectively released from TAED by reacting with peroxide under alkaline conditions. Thus, a cleaning agent which is most effective in the alkaline range is preferred for use with peracetic acid as a disinfectant and the peracetic acid is generated in situ. A particularly preferred cleaning agent is the subtilisin A enzyme, which is both effective under alkaline conditions and ophthalmically compatible under proper conditions. In addition, peracetic acid has been shown to have no significant interaction or detrimental effect on subtilisin, and vice versa.

Figure 1:
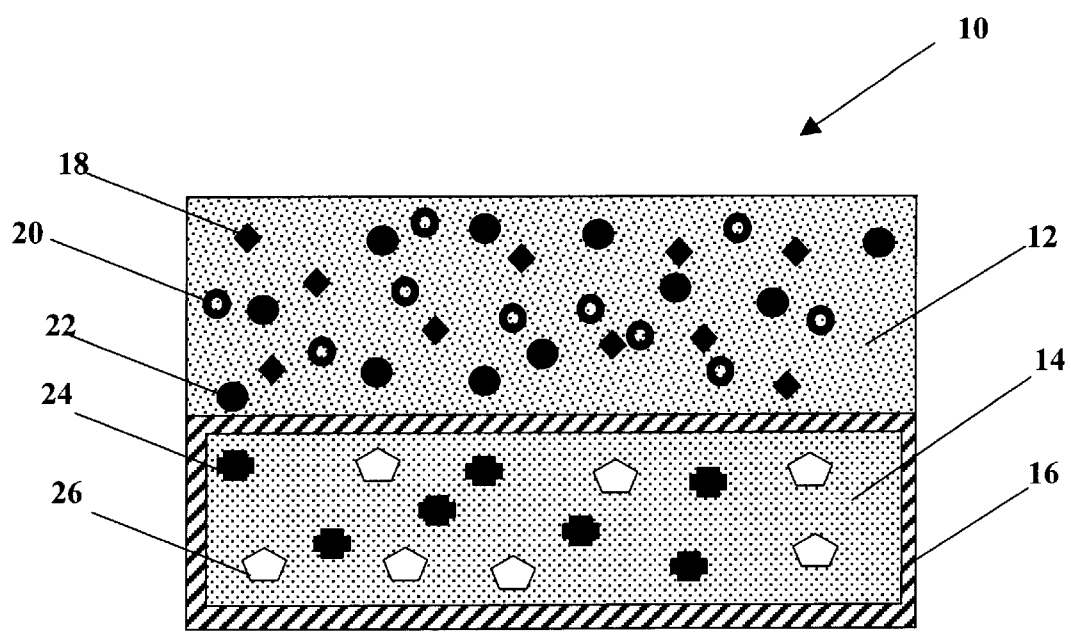
FIG. 1 is a side sectional view of a layered embodiment of the dosage form of the present invention.

FIG. 1 illustrates a side sectional view of a layered solid dosage form (or tablet) in accordance with one embodiment of the present invention. Solid dosage form 10 includes cleaning and disinfecting layer 12 and neutralizing layer 14 separated by delayed release layer 16. Cleaning and disinfecting portion 12 is a compressed tablet subsection which includes peroxide-generating means 18, activator 20 and cleaning agent 22. No external barrier circumscribes cleaning and disinfecting layer 12, thereby allowing dissolution initiation and action essentially immediately upon immersion of dosage form 10 into solution.

Neutralizing portion 14 includes means for neutralizing the disinfectant 24 and means for neutralizing the cleaning agent 26. These means may be the same or different. A preferred neutralizer for peracetic acid is ascorbic acid, while a stronger acid, such as tartaric acid or citric acidis preferred for to enhance speed of neutralization of the cleaning agent, thereby improving consumer convenience.

Delayed release means 16 surrounds neutralizing portion 14, inhibiting dissolution of the neutralizing means for a predetermined period of time to allow for sufficient cleaning and disinfecting to occur.

Figure 2:
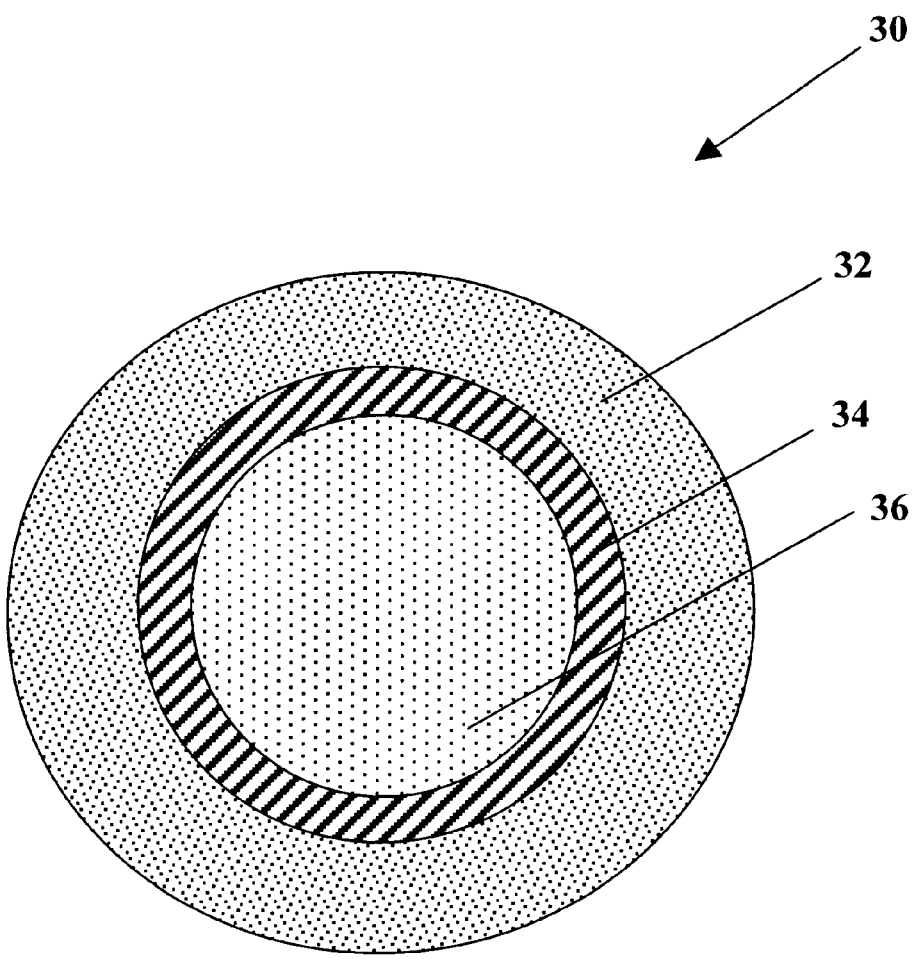
FIG. 2 is a side sectional view of a spherical embodiment of the dosage form of the present invention.

FIG. 2 illustrates an alternative tablet design which employs progressive concentric spheres. In this embodiment, cleaning and disinfecting portion 32 represents the outermost shell of a spherical dosage form, ensuring that the disinfectant and cleaning agent are dissolved first. Subsequent to portion 32 dissolution, delayed release portion 36 dissolves over a predetermined period of time to enable the formation of a concentrated and efficacious cleaning and disinfecting solution before neutralizing portion 34 dissolves.

Clearly, a person having ordinary skill in the art can conceive of various modifications of these embodiments, without departing from the spirit and scope of the invention. For example, a thin outer layer may be added to the entire device or merely the cleaning and disinfecting portion to enhance structural integrity or decomposition protection during storage, shipping and manual handling. Moreover, delayed release of neutralizer may be effected by microencapsulation of neutralizer and dispersement of the microencapsulated neutralizer within the cleaning and disinfecting portion, rather than fabricating a separate neutralization layer. Similarly, the delayed release layer may be absent in some areas, or completely non-existent under some conditions. Further, other known solid dosage form designs may be useful in accordance with the invention, such as, for example, osmotic pumps, such as those disclosed by Alza Corporation, Palo Alto, Calif. All such modifications are contemplated to be within the scope of the present invention.

In addition, either portion or layer may also include a means for enhancing or increasing the rate of dissolution. An exemplary means is an acid/base effervescent combination. Preferably, the cleaning and disinfecting portion includes a means for enhancing dissolution, in order to achieve maximum efficacy as quickly as possible after immersion in solution. While a number of effervescent combinations are known in the art, a citric acid or tartaric acid in combination with an alkali metal carbonate (especially sodium carbonate) is preferred.

The delayed release material may be selected from a number of materials known in the art for this purpose and which are ophthalmically compatible. A preferred class of delayed release polymer materials is polyvinyl alcohols. See U.S. Pat. No. 5,378,475, which is incorporated herein by reference, for further teaching on delayed release means.

The dosage form may also include other known ophthalmic excipients, such as tonicity enhancers, buffers and comfort-enhancing agents. Furthermore, additives useful in tablet manufacturing, such as lubricants (e.g., polyethylene glycols) or binders (e.g., lactose) may be included in the dosage form. In a preferred embodiment, the cleaning and disinfecting portion includes a PEG lubricant, while the neutralizing portion includes a lactose binder.

Considerations of consumer convenience dictate that, with the exception of the delayed release portion, dissolution times are maximized for the tablet. In a preferred embodiment, the cleaning and disinfecting layer dissolves in about 1 to 5 minutes, more preferably about 1 to 3 minutes and most preferably about 1.5 to 2.5 minutes. The delayed release layer preferably dissolves in about 1 to 25 minutes, more preferably about 5 to 20 minutes and most preferably about 10 to 15 minutes. Dissolution of the neutralizing portion preferably occurs in about 1 to 20 minutes, more preferably in about 5 to 15 minutes, and most preferably in about 8 to 12 minutes.

Clearly, the time of dissolution of the cleaning and disinfecting portion and delayed release portion are a function of the efficacy in microbe kill, and to a lesser extent, efficacy in protein and lipid deposit removal. Accordingly, concentrations and ingredient efficacy will affect the dissolution timing requirements in any specific design.

A complete cleaning and disinfecting system will utilize a container adapted to receive solution, contact lenses and the dosage form. An exemplary container is disclosed in U.S. Pat. No. 5,756,044, issued to Mowrey-McKee, et al., which is incorporated herein by reference. However, there are a number of possible container designs which can be advantageously used with the present invention. Further, the container does not require venting of gases produced during disinfection or effervescence, because the pressures developed by the presently disclosed systems are not extreme.

In operation, contact lenses will be placed into a lens-retaining means within the chosen container. Solution, such as a buffered saline solution, will be dispensed by the consumer into a container. The cleaning and disinfecting tablet may then be placed into the container, thereby initiating the cleaning and disinfecting process. Obviously, the order of these dispensing and placing steps is not critical.

The amount of solution which will be dispensed into the container can vary depending on a number of factors, such as the container volume limitations, consumer preference and desired concentration profiles. Preferably, about 5 to 20 milliliters of solution are used, more preferably about 8 to 15 ml, and most preferably about 10 ml.

For convenience, the dosage form components will be described on the basis of using 10 ml of buffered saline solution. As will be readily understood, dosage form composition must be adjusted, inter alia, depending on the target volume of solution and the solution type (buffered, saline, tap water). Remarkably, it has been shown that the present disinfecting components are sufficiently efficacious, when properly formulated, to operate with some tap water, which may contain a significant bioburden. However, preferably the consumer will utilized a controlled buffered, saline solution, so the dosage form will be described with respect to this preferred solution.

Upon dissolution of the disinfecting and cleaning portion, the TAED and perborate react vigorously to form peracetic acid, the disinfecting component, at basic conditions. Thus, once dissolved in solution, the pH of the solution should be basic. Preferably the pH is above about 8, more preferably between about 8.5 and 10.5, most preferably between about 8.5 and 9.5.

In addition, as mentioned earlier, a preferred enzyme for cleaning is subtilisin. Subtilisin functions more efficiently at a basic pH. In particular, a preferred pH range for subtilisin is about 8.5 to 10.

The effervescent couple (acid and base) in the tablet should be maintained at a relative concentration which will not impact the desired basic pH once the disinfecting and cleaning portion is dissolved in solution.

Thus, the dosage form includes a cleaning and disinfecting portion and a neutralizing portion. The cleaning and disinfecting portion preferably includes the following components: a peroxidegenerating species; an N,N-diacylamide activator; effervescent additives; an amount of enzyme sufficient to remove lipids and proteins from said lens, wherein said enzyme is strongly active in basic pH ranges and is relatively inactive at neutral pH ranges. The neutralizing portion will include a peracetic acid neutralizing means and an enzyme neutralizing means, which may be the same or different.

The cleaning portion preferably includes a proteolytic enzyme. A proteolytic enzyme will have in part or in total the capacity to hydrolyze peptide amide bonds. Such enzymes may also have some inherent lipolytic and/or amylolytic activity associated with the proteolytic activity.

Preferred proteolytic enzymes are those which are substantially free of sulfhydryl groups of disulfide bonds, whose presence may react with the active oxygen to the detriment of both the activity of the active oxygen and which may result in the untimely inactivation of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the more preferred enzymes are the Bacillus derived alkaline proteases generically called subtilisin enzymes. Reference is made to Deayl, L., Moser, P. W. and Wildi, B. S., "Proteases of the Genius Bacillus II alkaline Proteases" *Biotechnology* and *Bioengineering*, Vol. XII, pp 213–249 (1970) and Keay, L., and Moser, P. S., "Differentiation of Alkaline Proteases form Bacillus Species" *Biochemical* and *Biophysical* Research Comm., Vol 34, No. 5 pp 600–604, (1969).

The subtilisin enzymes are broken down into two sub-classes, subtilisin And subtilisin B. In the subtilisin A grouping are enzymes derived from such species are *B. subtilis, B. licheniformis* and *B. pumilis*. Organisms in this sub-class produce little or no neutral protease or amylase. The subtilisin B sub-class is made up of enzymes from such organisms as *B. subtilis, B. subtilis* var. amylosacchariticus, *B. amyloliquefaciens* and *B. subtilis* NRRL B3411. These organisms produce neutral proteases and amylases on a level about comparable to their alkaline protease production.

In addition, other preferred enzymes are, for example, pancreatin, trypsin, collaginase, keratinase, carboxylase, aminopeptidase, elastase, and aspergillo-peptidase. A and B, pronase (from *S. griseus*) and dispase from *Bacillus polymyxa*).

A preferred concentration of enzyme is about 0.1 mg to almost 10 mg per 10 ml. More preferable, the subtilisin concentration is about 0.5 to 2 mg per 10 ml.

In a preferred embodiment, the cleaning and disinfecting portion of the dosage form has the following composition, described in terms of weight/volume percentages (w/v %):

(a) about 0.2 to 2.0 w/v % sodium perborate monohydrate;

(b) about 0.05 to 1.0 w/v % tetraacetyl ethylene diamine (TAED);

(c) about 0.05 to 1.0 w/v % anhydrous citric acid;

(d) about 0.1 to 2.0 w/v % of a compound selected from the group consisting of sodium ascorbate, ascorbic acid and mixtures thereof; and (e) proteolytic enzyme.

In a more preferred embodiment, the dosage form has the following composition:

(a) about 0.5 to 1.5 w/v % sodium perborate monohydrate;

(b) about 0.1 to 0.75 w/v % tetraacetyl ethylene diamine (TAED);

(c) about 0.1 to 0.75 w/v % anhydrous citric acid;

(d) about 0.2 to 0.75 w/v % of a compound selected from the group consisting of sodium ascorbate, ascorbic acid and mixtures thereof; and (e) proteolytic enzyme.

In another more preferred embodiment, the dosage form has the following composition:

(a) about 1.0 to 1.2 w/v % sodium perborate monohydrate;

(b) about 0.25 to 0.5 w/v % tetraacetyl ethylene diamine (TAED);

(c) about 0.25 to 0.50 w/v % anhydrous citric acid;

(d) about 0.25 to 0.55 w/v % of a compound selected from the group consisting of sodium ascorbate, ascorbic acid and mixtures thereof; and (e) subtilisin.

In a particularly preferred embodiment, the dosage form has the following composition:

(a) about 0.65 w/v % sodium perborate monohydrate;

(b) about 0.25 w/v % tetraacetyl ethylene diamine (TAED);

(c) about 0.25 w/v % anhydrous citric acid;

(d) about 0.30 w/v % of a compound selected from the group consisting of sodium ascorbate, ascorbic acid and mixtures thereof; and (e) subtilisin.

An additional feature which may be added to the dosage form is a color indicator. An ophthalmically compatible indicator which changes color upon a change in pH from basic to acidic could be added to the cleaning and disinfecting portion. Upon dissolution of the cleaning and disinfecting portion, the pH is in the basic range and the color indicator could be one color indicating to the consumer that cleaning and disinfecting is occurring. Once the neutralizing portion has dissolved and the pH has dropped, the color indicator could change to another color (or clear—absence of color) to indicate to the consumer that it is safe to remove the contact lenses from the container.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, definitions or the like are provided to enhance the reader's comprehension of this document, and should not be read as limiting the scope of the present invention. Accordingly, the intellectual property rights to this invention are defined only by the following claims and reasonable extensions and equivalents thereof.

That which is claimed is:

1. A dosage form for cleaning and disinfecting, comprising:

(a) a first cleaning and disinfecting portion, including:

(1) a means for generating peracetic acid; and (2) a cleaning agent;

(b) a second neutralizing portion, including:
   (1) a means for neutralizing said peracetic acid;
   (2) a means for neutralizing said cleaning agent; and
   (3) a means for delayed release of said cleaning agent neutralization means and said peracetic acid neutralization means, wherein said first portion is affixed to said second portion.

2. A dosage form of claim 1, wherein said means for generating peracetic acid comprises:
   (a) a peroxide-generating species; and
   (b) an N,N-diacylamide activator.

3. A dosage form of claim 2, wherein said means for generating peracetic acid comprises:
   (1) sodium perborate monohydrate; and
   (2) tetraacetyl ethylene diamine.

4. A dosage form of claim 3, wherein said means for generating peracetic acid further comprises an effervescent couple.

5. A dosage form of claim 1, wherein said effervescent couple comprises:
   (a) anhydrous citric acid; and
   (b) a compound selected from the group consisting of sodium ascorbate, ascorbic acid and mixtures thereof.

6. A dosage form of claim 1, wherein said cleaning agent is a protease enzyme.

7. A dosage form of claim 6, wherein said cleaning agent is subtilisin.

8. A dosage form of claim 1, wherein said means for neutralizing said peracetic acid and means for neutralizing said cleaning agent are acids.

9. A dosage form of claim 8, wherein said means for neutralizing said peracetic acid is selected from the group consisting of ascorbic acid and sodium ascorbate.

10. A dosage form of claim 8, wherein said means for neutralizing said cleaning agent is an acid.

11. A dosage form of claim 1, wherein said a cleaning and disinfecting portion comprises:
   (a) about 0.2 to 2.0 w/v % sodium perborate monohydrate;
   (b) about 0.05 to 1.0 w/v % tetraacetyl ethylene diamine (TAED);
   (c) about 0.05 to 1.0 w/v % anhydrous citric acid;
   (d) about 0.1 to 2.0 w/v % of a compound selected from the group consisting of sodium ascorbate, ascorbic acid and mixtures thereof; and
   (e) proteolytic enzyme.

12. A dosage form of claim 11, wherein said a cleaning and disinfecting portion comprises:
   (a) about 0.5 to 1.5 w/v % sodium perborate monohydrate;
   (b) about 0.1 to 0.75 w/v % tetraacetyl ethylene diamine (TAED);
   (c) about 0.1 to 0.75 w/v % anhydrous citric acid;
   (d) about 0.2 to 0.75 w/v % of a compound selected from the group consisting of sodium ascorbate, ascorbic acid and mixtures thereof; and
   (e) proteolytic enzyme.

13. A dosage form of claim 12, wherein said a cleaning and disinfecting portion comprises:
   (a) about 1.0 to 1.2 w/v % sodium perborate monohydrate;
   (b) about 0.25 to 0.5 w/v % tetraacetyl ethylene diamine (TAED);
   (c) about 0.25 to 0.50 w/v % anhydrous citric acid;
   (d) about 0.25 to 0.55 w/v % of a compound selected from the group consisting of sodium ascorbate, ascorbic acid and mixtures thereof; and
   (e) subtilisin.

14. A method of disinfecting ophthalmic lenses, comprising the steps of:
   (a) forming an aqueous disinfecting solution comprising:
      (1) about 0.5 to 2.0 w/v % sodium perborate monohydrate;
      (2) about 0.1 to 1.0 w/v % tetraacetyl ethylene diamine; thereby generating peracetic acid in situ;
   (b) immersing an ophthalmic lens in the treatment solution to disinfect the lens; and
   (c) neutralizing said peracetic acid.

15. A method of cleaning and disinfecting ophthalmic lenses, comprising the steps of:
   (a) forming an aqueous cleaning and disinfecting solution comprising:
      (1) about 0.2 to 2.0 w/v % sodium perborate monohydrate;
      (2) about 0.05 to 1.0 w/v % tetraacetyl ethylene diamine; and
      (3) sufficient proteolytic enzyme to remove a substantial amount of protein and lipids from said opthalmic lenses;
   (b) immersing an ophthalmic lens in the treatment solution to clean and disinfect the lens; and
   (c) neutralizing said peracetic acid and enzyme.

16. A method of claim 15, comprising the steps of:
   (a) forming an aqueous cleaning and disinfecting solution comprising:
      (i) about 0.2 to 2.0 w/v % sodium perborate monohydrate;
      (ii) about 0.05 to 1.0 w/v % tetraacetyl ethylene diamine (TAED);
      (iii) about 0.1 to 0.75 w/v % anhydrous citric acid;
      (iv) about 0.1 to 0.75 w/v % of a compound selected from the group consisting of sodium ascorbate, ascorbic acid and mixtures thereof; and
      (v) sufficient proteolytic enzyme to remove a substantial amount of protein and lipids from said opthalmic lenses;
   (b) immersing an ophthalmic lens in the treatment solution to clean and disinfect the lens; and
   (c) neutralizing said peracetic acid and enzyme.

17. A method of claim 16, comprising the steps of:
   (a) forming an aqueous cleaning and disinfecting solution comprising:
      (i) about 0.5 to 2.0 w/v % sodium perborate monohydrate;
      (ii) about 0.25 to 0.50 w/v % tetraacetyl ethylene diamine (TAED);
      (iii) about 0.25 to 0.50 w/v % anhydrous citric acid;
      (iv) about 0.25 to 0.55 w/v % of a compound selected from the group consisting of sodium ascorbate, ascorbic acid and mixtures thereof; and
      (v) sufficient proteolytic enzyme to remove a substantial amount of protein and lipids from said opthalmic lenses;
   (b) immersing an ophthalmic lens in the treatment solution to clean and disinfect the lens; and
   (c) neutralizing said peracetic acid and enzyme.

* * * * *